United States Patent
Pan et al.

(10) Patent No.: US 11,369,951 B2
(45) Date of Patent: *Jun. 28, 2022

(54) CATALYST AND METHOD FOR PREPARING LIGHT OLEFIN USING DIRECT CONVERSION OF SYNGAS

(71) Applicant: DALIAN INSTITUTE OF CHEMICAL PHYSICS, CHINESE ACADEMY OF SCIENCES, Dalian (CN)

(72) Inventors: Xiulian Pan, Dalian (CN); Feng Jiao, Dalian (CN); Xinhe Bao, Dalian (CN); Na Li, Dalian (CN)

(73) Assignee: DALIAN INSTITUTE OF CHEMICAL PHYSICS, CAS, Dalian (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/963,181

(22) PCT Filed: Jan. 28, 2019

(86) PCT No.: PCT/CN2019/073384
§ 371 (c)(1),
(2) Date: Jul. 17, 2020

(87) PCT Pub. No.: WO2019/144950
PCT Pub. Date: Aug. 1, 2019

(65) Prior Publication Data
US 2021/0121859 A1    Apr. 29, 2021

(30) Foreign Application Priority Data
Jan. 26, 2018 (CN) .......................... 201810079238.6

(51) Int. Cl.
| | | |
|---|---|---|
| *B01J 35/00* | (2006.01) | |
| *B01J 21/04* | (2006.01) | |
| *B01J 21/06* | (2006.01) | |
| *B01J 23/06* | (2006.01) | |
| *B01J 23/08* | (2006.01) | |
| *B01J 23/10* | (2006.01) | |
| *B01J 23/18* | (2006.01) | |
| *B01J 23/26* | (2006.01) | |
| *B01J 23/34* | (2006.01) | |
| *B01J 23/745* | (2006.01) | |
| *B01J 23/75* | (2006.01) | |
| *B01J 29/70* | (2006.01) | |
| *B01J 29/76* | (2006.01) | |

(Continued)

(52) U.S. Cl.
CPC .......... *B01J 35/0006* (2013.01); *B01J 21/04* (2013.01); *B01J 21/066* (2013.01); *B01J 23/06* (2013.01); *B01J 23/08* (2013.01); *B01J 23/10* (2013.01); *B01J 23/18* (2013.01); *B01J 23/26* (2013.01); *B01J 23/34* (2013.01); *B01J 23/745* (2013.01); *B01J 23/75* (2013.01); *B01J 29/70* (2013.01); *B01J 29/7015* (2013.01); *B01J 29/7065* (2013.01); *B01J 29/763* (2013.01); *B01J 29/83* (2013.01); *B01J 29/84* (2013.01); *B01J 29/85* (2013.01); *B01J 29/87* (2013.01); *B01J 35/1014* (2013.01); *B01J 35/1019* (2013.01); *C07C 1/043* (2013.01); *C07C 2523/06* (2013.01); *C07C 2523/08* (2013.01); *C07C 2523/10* (2013.01); *C07C 2523/18* (2013.01); *C07C 2523/26* (2013.01); *C07C 2523/34* (2013.01)

(58) Field of Classification Search
CPC .... B01J 29/7065; B01J 29/7015; B01J 29/70; B01J 23/75; B01J 23/745; B01J 23/34; B01J 23/26; B01J 23/18; B01J 23/10; B01J 23/08; B01J 23/06; B01J 21/066; B01J 21/04; B01J 35/0006; C07C 1/043; C07C 2523/06; C07C 2523/08; C07C 2523/10; C07C 2523/18; C07C 2523/26; C07C 2523/34

See application file for complete search history.

(56) References Cited

U.S. PATENT DOCUMENTS

2007/0244000 A1    10/2007  Molinier et al.
2011/0201860 A1*   8/2011   Akhtar .................... C07C 2/76
                                                        585/419

FOREIGN PATENT DOCUMENTS

CN    104760975 A    7/2015
CN    105087042 A    11/2015

OTHER PUBLICATIONS

Feng Jiao, et al., "Selective conversion of syngas to light olefins", Science, Mar. 14, 2016 • vol. 351 Issue 6277, pp. 1065-1068.
International Search Report dated Apr. 2, 2019 for related International Patent Application No. PCT/CN2019/073384 issued by the international searching authority.

(Continued)

*Primary Examiner* — Jafar F Parsa
(74) *Attorney, Agent, or Firm* — MagStone Law, LLP; Enshan Hong

(57) ABSTRACT

A catalyst for preparing light olefin using direct conversion of syngas is a composite catalyst and formed by compounding component I and component II in a mechanical mixing mode. The active ingredient of component I is a metal oxide; and the component II is one or more than one of zeolite of CHA and AEI structures or metal modified CHA and/or AEI zeolite. A weight ratio of the active ingredients in the component I to the component II is 0.1-20. The reaction process has high product yield and selectivity, wherein the sum of the selectivity of the propylene and butylene reaches 40-75%; and the sum of the selectivity of light olefin comprising ethylene, propylene and butylene can reach 50-90%. Meanwhile, the selectivity of a methane side product is less than 15%.

14 Claims, No Drawings

(51) Int. Cl.
*B01J 29/83* (2006.01)
*B01J 29/84* (2006.01)
*B01J 29/85* (2006.01)
*B01J 29/87* (2006.01)
*B01J 35/10* (2006.01)
*C07C 1/04* (2006.01)

(56) References Cited

OTHER PUBLICATIONS

Written Opinion dated Apr. 3, 2019 for related International Patent Application No. PCT/CN2019/073384 issued by the international searching authority.

* cited by examiner

CATALYST AND METHOD FOR PREPARING LIGHT OLEFIN USING DIRECT CONVERSION OF SYNGAS

RELATED APPLICATIONS

This is a U.S. national stage of international application No. PCT/CN2019/073384 filed on Jan. 28, 2019, which claims priority from China Patent Application No. 201810079238.6 filed on Jan. 26, 2018, the entire content of which is incorporated herein as reference.

TECHNICAL FIELD

The present invention belongs to preparation of light olefin using syngas, and particularly relates to a catalyst and a method for preparing light olefin using direct conversion of syngas.

BACKGROUND

Light olefin refers to alkene with the number of carbon atoms less than or equal to 4. Light olefin represented by ethylene and propylene are very important basic organic chemical raw materials. With the fast growth of economy in China, the market of the light olefin is in short supply for a long time. At present, the light olefin is produced mainly through a petrochemical route of cracking of light hydrocarbon (ethane, naphtha and light diesel fuel). Due to the increasing shortage of global petroleum resources and the long-term high-price operation of crude oil, the development of the light olefin industry relying only on a tubular cracking furnace technology that uses petroleum light hydrocarbon as raw material will encounter more and more difficulties in raw material. The production technology and the raw material of the light olefin must be diversified. A technology for preparing alkene using syngas can widen the source of the raw material, and will provide an alternative solution for a steam cracking technology based on high-cost raw material such as naphtha by production of syngas using crude oil, natural gas, coal and renewable material as raw material. One-step direct preparation of the light olefin using the syngas is a process of directly preparing the light olefin with the number of carbon atoms less than or equal to 4 through Fischer-Tropsch synthesis reaction of carbon monoxide and hydrogen under the action of the catalyst. This process simplifies the process flow and greatly reduces the investment unlike an indirect method that further prepares the alkene from the syngas and the methanol or dimethyl ether.

Direct preparation of the light olefin using the syngas through Fischer-Tropsch synthesis has become one of research hotspots in development of catalyst for Fischer-Tropsch synthesis. In patent CN1083415A disclosed by Dalian Institute of Chemical Physics, Chinese Academy of Sciences, high activity (CO conversion rate: 90%) and selectivity (light olefin selectivity: 66%) can be obtained under reaction pressure of 1.0 to 5.0 MPa and reaction temperature of 300 to 400° C. in preparation of the light olefin from the syngas under the auxiliary of alkali K or Cs ion by using an iron-manganese catalyst system carried by IIA alkali metal oxide such as MgO or silica rich zeolite (or phosphorous-aluminum zeolite). In patent ZL03109585.2 declared by Beijing University Of Chemical Technology, Fe/activated carbon catalyst with manganese, copper, zinc, silicon and potassium as auxiliaries is prepared by a vacuum impregnation method for the reaction of preparation of the light olefin from the syngas. Under the condition of no feedstock gas circulation, the CO conversion rate is 96%, and the selectivity of the light olefin in hydrocarbons is 68%. Recently, professor de Jong's team at Utrecht university in Netherlands made good progress by using Fe catalyst modified by Fe, Na, S and other auxiliaries supported by SiC, carbon nanofiber and other inert carriers, obtained 61% of selectivity of lower alkene. However, the selectivity is reduced when the conversion rate is increased. In direct preparation of the alkene using the syngas, because raw material of CO and $H_2$ are gaseous and the ethylene in a target product has a low boiling point, cryogenic separation is needed generally. If the alkene containing three carbon atoms or four carbon atoms is obtained with high selectivity, i.e., $C_3$-$C_4$ alkene product of propylene and butylene, cryogenic separation is not needed, thereby greatly reducing energy consumption and cost for separation and bringing great application value. In the above report, the catalyst uses metal iron or iron carbide as the active component. The reaction follows the chain growth mechanism of metal surfaces. The selectivity of the product lower alkene is low, while the selectivity of $C_3$-$C_4$ alkene is lower.

Recently, a composite bifunctional catalyst of $ZnCr_2O_4$ oxide and hierarchical pore SAPO-34 zeolite has been reported by academician Bao Xinhe and researcher Pan Xiulian in Dalian Institute of Chemical Physics, Chinese Academy of Sciences (Jiao et al., Science 351 (2016) 1065-1068), which has realized 80% of selectivity of the light olefin when the conversion rate of CO is 17%, wherein the selectivity of the light olefin is 14 and the alkene/alkane ratio is 5.7. When the conversion rate is increased to 35%, the alkene selectivity is 69%, alkane selectivity is 20%, alkene/alkane ratio is decreased to 3.5 and propylene and butylene selectivity is 40-50%.

SUMMARY OF THE INVENTION

In view of the above problems, the present invention provides a catalyst and a method for preparing light olefin using direct conversion of syngas.

The technical solution of the present invention is: a catalyst comprises component I and component II; the component I and the component II are compounded in a mechanical mixing mode; an active ingredient of the component I is a metal oxide; the component II is a zeolite of CHA or AEI topology; the metal oxide is one or more than one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$ and $In_aGa_bMn_{(1-a-b)}O_x$.

The specific surface area of $MnO_x$, $ZnO_x$, $CeO_x$, $GaO_x$, $BiO_x$ and $InO_x$ is 1-100 m²/g; and a preferred specific surface area is 50-100 m²/g.

The specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn_{(1-a-b)}O_x$ and $In_aGa_bMn_{(1-a-b)}O_x$ is 5-150 m²/g; and a preferred specific surface area is 50-150 m²/g.

The value range of x is 0.7-3.7, and the value range of a is 0-1; and the value range of a+b is 0-1.

a, b, (1-a), (1-a-b) and x in the present invention only represent the relative proportions of the chemical composition of the elements in the metal oxide. Any metal oxide with the same proportion is regarded as the same metal oxide.

The zeolite of CHA and AEI topology in the present invention has eight-membered ring orifices and a three-dimensional porous channel and comprises cha cage.

The skeleton element composition of the zeolite of CHA and AEI topologies may be one or more than one of Si—O, Si—Al—O, Si—Al—P—O, Al—P—O, Ga—P—O, Ga—Si—Al—O, Zn—Al—P—O, Mg—Al—P—O and Co—Al—P—O.

The zeolite of the component II has mediate strong acid sites, and the amount of the mediate strong acid sites is 0-0.3 mol/kg, preferably 0.003-0.2 mol/kg, and more preferably 0.003-0.06 mol/kg.

The peak temperature range corresponding to a desorption peak of $NH_3$-TPD for mediate strong acid in the present invention is 275-500° C. The acid intensity is defined by $NH_3$-TPD, including three kinds of acid: weak acid, mediate strong acid and strong acid. The $NH_3$-TPD is the position of a desorption peak according to $NH_3$; the position of the desorption peak means that under standard test conditions that a ratio of sample mass w and carrier gas flow rate f (w/f) is 100 g·h/L and a heating rate is 10° C./min, a TCD records a thermal conductivity signal of desorption of $NH_3$ and draws a desorption curve; according to peaks in positions of curve peaks, the inorganic solid is divided into three acid intensities; the weak acid is an acid site where the deposition temperature of $NH_3$ is less than 275° C.; the mediate strong acid is an acid site where the deposition temperature of $NH_3$ is between 275° C. and 500° C.; and the strong acid is an acid site where the deposition temperature of $NH_3$ is greater than 500° C.

By using acetone as a probe molecule, the chemical displacement of $^{13}C$-NMR is in the range of 210-220 ppm.

A weight ratio of the active ingredients in the component I to the component II is 0.1-20, and preferably 0.3-5.

A dispersing agent is also added to the component I; the metal oxide is dispersed in the dispersing agent; and the dispersing agent is one or more than one of $Al_2O_3$, $SiO_2$, $Cr_2O_3$, $ZrO_2$, $TiO_2$, $Ga_2O_3$, activated carbon, graphene and carbon nanotube.

In the component I, the content of the dispersing agent is 0.05-90 wt %, and the balance is the metal oxide.

H (hydrogen) may be connected or not connected to O element of the zeolite skeleton of the component II; and the H may be entirely or partially replaced by one or more than one of Na, Ca, K, Mg, Ge, Zr, Zn, Cr, Ga, Sn, Fe, Co, Mo and Mn by ion exchange, and the total molar ratio of the substitute metal to oxygen is 0.0002-0.001.

Another aspect of the present invention provides a method for preparing light olefin using direct conversion of syngas, wherein syngas is used as reaction raw material; a conversion reaction is conducted on a fixed bed or a moving bed; and the adopted catalyst is the catalyst of any one of claims 1-5.

The pressure of the syngas is 0.5-10 MPa, and preferably 1-8 MPa; reaction temperature is 300-600° C., and preferably 350° C.-450° C.; space velocity is 300-12000 $h^{-1}$, preferably 1000-9000 $h^{-1}$ and more preferably 3000-9000 $h^{-1}$; the syngas is $H_2$/CO mixture; and the ratio of $H_2$/CO is 0.2-3.5, and preferably 0.3-2.5.

The catalyst in the present invention is used for preparing light olefin using one-step direct conversion of syngas, wherein the selectivity for propylene and butylene is 40-75%, and preferably 50-75%, while the selectivity for a methane side product is lower than 15%, and preferably less than 10%.

The present invention has the following advantages:

1. Different from the traditional technology for preparing the light olefin through methanol (MTO for short), this technology realizes preparation of the light olefin through one-step direct conversion of syngas.

2. Propylene and butylene selectivity is as high as 40-75%. The products are separated without deep cooling, thereby greatly reducing separation energy consumption and cost.

3. The active ingredient metal oxide of the component I in the catalyst has a higher specific surface area; therefore, the metal oxide surface has more active sites, which is more conducive to conducting a catalytic reaction.

4. On one hand, the role of the component II in the catalyst is to further convert the active gas-phase intermediate produced by the component I to obtain light olefin by coupling with the component I. The role of the component II on the balanced pull of the series reaction can promote the activation and conversion of the component I for the syngas and thus can increase the conversion rate. On the other hand, the special porous channel structure of the zeolite in the component II used in the present invention has a unique selection effect and can obtain more light olefin products with high selectivity.

5. The functions of the present invention cannot be achieved if the component I or the component II in the present invention is used separately. For example, the selectivity of methane in the product after separate use of the component I is very high, and the conversion rate is very low. The syngas cannot be activated and converted if the component II is used separately. Only the synergistic catalysis of the component I and the component II can achieve efficient conversion of the syngas and obtain excellent selectivity. Because the component I can activate the syngas to generate a specific active gas-phase intermediate, the intermediate diffuses into the porous channel of the component II through the gas phase. The zeolite of the CHA or AEI topology selected in the present invention has special pore structure and acidity which can effectively further activate and convert the active gas-phase intermediate produced by the component I into olefin. The special porous channel structure of the component II enables the product to have special selectivity.

6. The preparation process of the composite catalyst of the present invention is simple and has mild conditions. The reaction process has an extremely high product yield and selectivity, with the selectivity for $C_2$-$C_4$ light olefin reaching 50-90% and especially high selectivity for $C_3$-$C_4$ olefin. Meanwhile, the selectivity for a methane side product is low (<15%), and the catalyst has long service life which is greater than 700 hours. The present invention has excellent application prospect.

DETAILED DESCRIPTION OF PREFERRED EMBODIMENTS

The present invention is further illustrated below by embodiments, but the scope of claims of the present invention is not limited by the embodiments. Meanwhile, the embodiments only give some conditions for achieving the purpose, but it does not mean that the conditions must be satisfied to achieve the purpose.

The specific surface area of the sample can be tested through a physical adsorption method of nitrogen or argon.

The metal oxide in the present invention can be obtained by purchasing a commercially available metal oxide with a high specific surface area, or by the following methods:

I. Preparation of Component I of Catalyst (I) ZnO material with high specific surface area was synthesized through a precipitation method:

(1) 3 parts of 0.446 g (1.5 mmol) of $Zn(NO_3)_2.6H_2O$ were respectively weighed into three containers; 0.300 g (7.5 mmol), 0.480 g (12 mmol) and 0.720 g (18 mmol) of NaOH were respectively weighed and successively added to the above three containers; 30 ml of deionized water was weighed and added to the three containers; stirring was conducted for a time greater than 0.5 h at 70° C. to uniformly mix a solution; natural cooling was conducted to room temperature; reaction liquid was centrifugally separated to collect the centrifugally separated precipitate; and washing was conducted with deionized water twice to obtain ZnO metal oxide precursor;

(2) roasting: after drying the obtained product in the air, the product was roasted in an atmosphere to obtain ZnO material with high specific surface area. The atmosphere is inert gas, reducing gas or oxidizing gas. The inert gas is one or more than one of $N_2$, He and Ar. The reducing gas is one or two of $H_2$ and CO, and the reducing gas may also contain the inert gas. The oxidizing gas is one or more than one of $O_2$, $O_3$ and $NO_2$, and the oxidizing gas may also contain the inert gas. Roasting temperature is 300-700° C., and time is 0.5 h-12 h.

The purpose of roasting is to decompose the precipitated metal oxide precursor into oxide nanoparticles with high specific surface area at high temperature, and clean the adsorbed species on the surface of the oxide generated by decomposition through the high temperature roasting treatment.

Specific samples and preparation conditions thereof are shown in Table 1 below. As a reference example, ZnO#4 in the table is a commercially available ZnO single crystal with low specific surface area.

TABLE 1

Preparation of ZnO Material and Parameter Performance

| Zinc Oxide Sample Number | Roasting Time/h | Roasting Temperature/° C. | Roasting Atmosphere | Specific Surface Area $m^2/g$ |
|---|---|---|---|---|
| ZnO#1 | 5 | 500 | Ar | 71 |
| ZnO#2 | 2 | 320 | 5% $H_2/N_2$ | 47 |
| ZnO#3 | 3 | 550 | Air | 15 |
| ZnO#4 | — | — | | <1 |

(II) MnO material with high specific surface area was synthesized through a coprecipitation method:

The preparation process is the same as that of the above ZnO#2. The difference is that, the precursor of Zn is changed for the corresponding precursor of Mn, which may be one of manganous nitrate, manganese chloride and manganese acetate, and is manganous nitrate herein. The corresponding product is defined as MnO. The specific surface area is 23 $m^2/g$.

(III) $CeO_2$ material with high specific surface area was synthesized through a coprecipitation method:

The preparation process is the same as that of the above ZnO#2. The difference is that, the precursor of Zn is changed for the corresponding precursor of Ce, which may be one of cerium nitrate, cerium chloride and cerous acetate, and is cerium nitrate herein. The corresponding product is defined as $CeO_2$. The specific surface area is 92 $m^2/g$.

(IV) $Ga_2O_3$ material with high specific surface area was synthesized through a coprecipitation method:

The preparation process is the same as that of the above ZnO#2. The difference is that the precursor of Zn is changed for the corresponding precursor of Ga, which may be one of gallium nitrate, gallium chloride and gallium acetate, and is gallium nitrate herein. The corresponding product is defined as $Ga_2O_3$. The specific surface area is 55 $m^2/g$.

(V) $Bi2O_3$ material with high specific surface area was synthesized through a coprecipitation method:

The preparation process is the same as that of the above ZnO#2. The difference is that the precursor of Zn is changed for the corresponding precursor of Bi, which may be one of bismuth nitrate, bismuth chloride and bismuth acetate, and is bismuth nitrate herein. The corresponding product is defined as $Bi_2O_3$. The specific surface area is 87 $m^2/g$.

(VI) $In_2O_3$ material with high specific surface area was synthesized through a coprecipitation method:

The preparation process is the same as that of the above ZnO#2. The difference is that the precursor of Zn is changed for the corresponding precursor of In, which may be one of indium nitrate, indium chloride and indium acetate, and is indium nitrate herein. The corresponding product is defined as $In_2O_3$. The specific surface area is 52 $m^2/g$.

(VII) $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CO_aAl_{(1-a)}O_x$, $Fe_aAl_{(1-a)}O_x$, $In_aAl_bMn_{(1-a-b)}O_x$ and $In_aGa_bMn_{(1-a-b)}O_x$ with high specific surface area were synthesized through a precipitation method:

Zinc nitrate, aluminum nitrate, chromic nitrate, manganese nitrate, zirconium nitrate, indium nitrate, cobalt nitrate and ferric nitrate were adopted as precursors, and mixed at room temperature in water (wherein for ammonium carbonate as a precipitant, a feeding ratio is excessive or the ratio of ammonium ions to metal ions is preferably 1:1); The above mixed solution was aged, and then taken out for washing, filtering and drying; and the obtained solid is roasted under an air atmosphere to obtain a metal oxide with high specific surface area. Specific samples and preparation conditions thereof are shown in Table 2 below.

TABLE 2

Preparation of Metal Oxide with High Specific Surface Area and Performance Parameters

| Metal Oxide | Feeding Ratio of Metal Elements and Final Molar Concentration of One Metal in Water (mmol/L) | Aging Temperature° C. | Aging Time h | Roasting Temperature° C. | Roasting Time h | Specific Surface Area $m^2/g$ |
|---|---|---|---|---|---|---|
| $ZnCr_2O_4$ | ZnCr = 1:2, and Zn is 50 mM | 120 | 24 | 500 | 2 | 126 |
| $ZnAl_2O_4$ | ZnAl = 1:2, and Zn is 50 mM | 130 | 20 | 400 | 4 | 137 |
| $ZnGa_2O_4$ | ZnGa = 1:2, and Zn is 50 mM | 130 | 20 | 400 | 4 | 110 |
| $ZnIn_2O_4$ | ZnIn = 1:2, and Zn is 50 mM | 130 | 20 | 400 | 4 | 87 |
| $MnCr_2O_4$ | MnCr = 1:2, and Mn is 50 mM | 140 | 18 | 450 | 3 | 11 |
| $MnAl_2O_4$ | MnAl = 1:2, y = 2; and Mn is 50 mM | 145 | 16 | 400 | 2 | 15 |

TABLE 2-continued

Preparation of Metal Oxide with High Specific Surface Area and Performance Parameters

| Metal Oxide | Feeding Ratio of Metal Elements and Final Molar Concentration of One Metal in Water (mmol/L) | Aging Temperature° C. | Aging Time h | Roasting Temperature° C. | Roasting Time h | Specific Surface Area $m^2/g$ |
|---|---|---|---|---|---|---|
| $MnZr_2O_4$ | MnZr = 1:2, and Mn is 50 mM | 150 | 12 | 500 | 1 | 38 |
| $MnIn_2O_4$ | MnIn = 1:2, and Mn is 50 mM | 150 | 12 | 500 | 1 | 67 |
| $CoAl_2O_4$ | CoAl = 1:2, and Co is 50 mM | 145 | 16 | 400 | 2 | 22 |
| $FeAl_2O_4$ | FeAl = 1:2, and Fe is 50 mM | 145 | 16 | 400 | 2 | 30 |
| $InAl_3MnO_7$ | In:Al:Mn = 1:3:1; and Mn is 50 mM | 150 | 12 | 500 | 1 | 84 |
| $InGa_2MnO_7$ | In:Ga:Mn = 1:2:1; and Mn is 50 mM | 145 | 16 | 400 | 2 | 67 |

(VIII) Metal oxide dispersed in dispersing agent $Cr_2O_3$, $Al_2O_3$ or $ZrO_2$ $Cr_2O_3$, $Al_2O_3$ or $ZrO_2$ dispersed metal oxide was prepared through a precipitate deposition method by taking $Cr_2O_3$, $Al_2O_3$ or $ZrO_2$ as a carrier. The preparation of dispersed ZnO was taken as an example (the specific surface area is about 5 $m^2/g$)

Commercial $Cr_2O_3$, $Al_2O_3$ (the specific surface area is about 20 $m^2/g$) or $ZrO_2$ (the specific surface area is about 10 $m^2/g$) as a carrier was dispersed in water in advance, and then mixed and precipitated at room temperature with a sodium hydroxide precipitant by taking zinc nitrate as raw material. The molar concentration of $Zn^{2+}$ is 0.067M; and the ratio of molar fractions of $Zn^{2+}$ and the precipitant is 1:8; and then aging was conducted at 160° C. for 24 hours to obtain dispersed ZnO by taking $Cr_2O_3$, $Al_2O_3$ or $ZrO_2$ as the carrier (the contents of the dispersing agents in the component I are 0.1 wt %, 20 wt % and 85 wt %). The obtained sample was roasted at 500° C. for 1 hour in air. The products were successively defined as dispersed oxides 1-3, and the specific surface areas were successively 148 $m^2/g$, 115 $m^2/g$ and 127 $m^2/g$.

The same method is used to obtain dispersed MnO oxide by taking $SiO_2$ (the specific surface area is about 2 $m^2/g$), $Ga_2O_3$ (the specific surface area is about 10 $m^2/g$), or $TiO_2$ (the specific surface area is about 15 $m^2/g$) as the carrier (the contents of the dispersing agents in the component I are 5 wt %, 30 wt % and 60 wt %). The products are successively defined as dispersed oxides 4-6. The specific surface areas are successively 97 $m^2/g$, 64 $m^2/g$ and 56 $m^2/g$.

The same method is used to obtain dispersed ZnO oxide by taking activated carbon (the specific surface area is about 1000 $m^2/g$), graphene (the specific surface area is about 500 $m^2/g$), or carbon nanotube (the specific surface area is about 300 $m^2/g$) as the carrier (the contents of the dispersing agents in the component I are 5 wt %, 30 wt % and 60 wt %). The products are successively defined as dispersed oxides 7-9. The specific surface areas are successively 177 $m^2/g$, 245 $m^2/g$ and 307 $m^2/g$. II. Preparation of component II (zeolite of CHA and AEI topology):

The CHA and AEI topology has eight-membered ring orifices and a three-dimensional porous channel and comprises cha cage.

The mediate strong acid described in the present invention can be tested by solid nuclear magnetic H spectrum, $NH_3$-TPD, infrared ray and chemical titration. However, the test method of the acidity is not limited to the above test methods.

The zeolite in the present invention may be the zeolite of CHA and AEI topology having acid density that satisfies the requirements of the present invention, and may also be the zeolite prepared according to the method reported in the existing literature (Chemcatchem, 2012, 4, 1428-1435). The present invention takes the zeolite prepared by a hydrothermal synthesis method as an example.

1) The specific preparation process is as follows:

The raw materials of 30% (mass concentration) of silica sol, AlOOH, phosphoric acid, TEA® and deionized water were weighed according to oxide $SiO_2:Al_2O_3:H_3PO_4:R:H_2O=1.6:16:32:55:150$ (mass ratio); after mixing at room temperature, 0.5 time of molar weight of auxiliary HF was added to a template agent; the mixture was stirred and aged at 30° C. and then transferred into a hydrothermal reactor after 2 h, and crystallized at 200° C. for 24 h. The water bath was quenched to room temperature. Centrifugal washing was conducted repeatedly so that the pH of the supernatant is 7 at the end of washing. After the precipitate was dried at 110° C. for 17 h, the precipitate was calcined in air at 600° C. for 3 h to obtain the silicon-phosphorus-aluminum inorganic solid acid with hierarchical pore structure.

The skeleton element composition of the zeolite of CHA and AEI topologies may be one or more than two of Si—O, Si—Al—O, Si—Al—P—O, Al—P—O, Ga—P—O, Ga—Si—Al—O, Zn—Al—P—O, Mg—Al—P—O and Co—Al—P—O.

O element of part of the skeleton is connected with H, and corresponding products are successively defined as parts 1-7.

TABLE 3

Preparation of Zeolite of CHA or AEI Topology and Performance Parameters

| Zeolite Sample Number | Si Source | Aluminum Source | p Source | Template Agent | Auxiliary | Mass Ratio | Hydrothermal Temperaturer/° C. | Time/day | Acid Amount mol/kg |
|---|---|---|---|---|---|---|---|---|---|
| part 1 | TEOS | sodium metaaluminate | phosphoric acid | TEA | | $SiO_2:Al_2O_3:H_3PO_4:R:H_2O = 1.6:16:32:55:150$ | 180 | 1 | 025 |

TABLE 3-continued

Preparation of Zeolite of CHA or AEI Topology and Performance Parameters

| Zeolite Sample Number | Si Source | Aluminum Source | p Source | Template Agent | Auxiliary | Mass Ratio | Hydrothermal Temperaturer/° C. | Time/day | Acid Amount mol/kg |
|---|---|---|---|---|---|---|---|---|---|
| part 2 | silica sol | Al(OH)$_3$ | phosphoric acid | Mor | HCl | SiO$_2$:Al$_2$O$_3$:H$_3$PO$_4$:R:H$_2$O = 2.4:19:30:15:150 | 150 | 4 | 027 |
| part 3 | TEOS | AlOOH | phosphoric acid | TEAOH | HF | SiO$_2$:Al$_2$O$_3$:H$_3$PO$_4$:R:H$_2$O = 0.7:15:32:55:150 | 160 | 4 | 0.13 |
| part 4 | silica sol | aluminum isopropoxide | phosphoric acid | DIPEA | | SiO$_2$:Al$_2$O$_3$:H$_3$PO$_4$:R:H$_2$O = 1.1:17:32:55:150 | 170 | 2.5 | 023 |
| part 5 | | aluminum sulfate | phosphoric acid | TEAOH | HF | Al$_2$O$_3$:H$_3$PO$_4$:R:H$_2$O = 16:32:55:150 | 190 | 1 | 0.006 |
| part 6 | silica sol | aluminum nitrate | phosphoric acid | DIPEA | | SiO$_2$:Al$_2$O$_3$:H$_3$PO$_4$:R:H$_2$O = 0.5:17:32:55:150 | 200 | 1 | 0.078 |
| part 7 | TEOS | aluminum sulfate | phosphoric acid | TEA | HF | SiO$_2$:Al$_2$O$_3$:H$_3$PO$_4$:R:H$_2$O = 0.3:18:32:55:150 | 170 | 0.7 | 0.055 |
| part 8 | | aluminum nitrate | phosphoric acid | TEA | HCl | Al$_2$O$_3$:H$_3$PO$_4$:R:H$_2$O = 11:32:55:150 | 160 | 3.5 | 0.014 |

2) The H connected to the O element of skeletons of the above products 1-8 is replaced by the following metal ion parts: Na, Ca, K, Mg, Ge, Zr, Zn, Cr, Ga, Sn, Fe, Co, Mo and Mn by ion exchange; and the preparation process is:

The above samples of parts 1-8 were taken and then mixed with 0.5 mol/L of metal ion nitrate solution to be exchanged according to the solid-liquid mass ratio of 1:30. The mixture was stirred at 80° C. for 6 h, washed, dried twice continuously, and roasted at 550° C. for 3 h to obtain CHA or AEI after metal ion exchange.

Corresponding products are successively defined as parts 9-22.

TABLE 4

Preparation of Zeolite of CHA or AEI Topology and Performance Parameters

| Zeolite Sample Number | Ion | Ratio of metal ion and O | Zeolite to be Exchanged | Exchange Temperature/° C. | Time/h | Acid Amount mol/kg |
|---|---|---|---|---|---|---|
| part 9 | Na | 0.04 | part 1 | 80 | 8 | 0.23 |
| part 10 | Ca | 0.02 | part 2 | 90 | 7 | 0.03 |
| part 11 | K | 0.01 | part 3 | 80 | 7 | 0.11 |
| part 12 | Mg | 0.015 | part 4 | 90 | 5 | 0.08 |
| part 13 | Ge | 0.075 | part 5 | 80 | 7 | 0.15 |
| part 14 | Zr | 0.03 | part 6 | 90 | 7 | 0.05 |
| part 15 | Zn | 0.005 | part 7 | 80 | 8 | 0.10 |
| part 16 | Cr | 0.07 | part 8 | 70 | 3 | 0.25 |
| part 17 | Ga | 0.01 | part 1 | 80 | 6 | 0.17 |
| part 18 | Sn | 0.001 | part 2 | 60 | 5 | 0.27 |
| part 19 | Fe | 0.0005 | part 3 | 70 | 5 | 0.23 |
| part 20 | Co | 0.0003 | part 4 | 80 | 6 | 0.18 |
| part 21 | Mo | 0.0005 | part 5 | 70 | 3 | 0.28 |
| part 22 | Mn | 0.002 | part 6 | 70 | 8 | 0.29 |

3) Zeolite composed of other elements

| Sample Number | Precursor 1 | Precursor 2 | Precursor 3 | Template Agent | Auxiliary | Mass Ratio | Hydrothermal Temperature (° C.) | Time (Day) | Acid Amount mol/kg |
|---|---|---|---|---|---|---|---|---|---|
| part 23 | TEOS | | | TEA | HF | SiO$_2$:R:H$_2$O = 1.6:55:150 | 180 | 1 | 0.004 |
| part 24 | silica sol | Al(OH)$_3$ | | Mor | HF | SiO$_2$:Al$_2$O$_3$:R:H$_2$O = 2.4:19:15:150 | 150 | 4 | 0.11 |
| part 25 | | gallium nitrate | phosphoric acid | TEAOH | HF | Ga$_2$O$_3$:H$_3$PO$_4$:R:H$_2$O = 15:32:55:150 | 160 | 4 | 0.012 |
| part 26 | silica sol | gallium nitrate | phosphoric acid | TEA | HF | SiO$_2$:Ga$_2$O$_3$:H$_3$PO$_4$:R:H$_2$O = 1.1:17:32:55:150 | 170 | 2.5 | 0.07 |

-continued

| Sample Number | Precursor 1 | Precursor 2 | Precursor 3 | Template Agent | Auxiliary | Mass Ratio | Hydrothermal Temperature (° C.) | Time (Day) | Acid Amount mol/kg |
|---|---|---|---|---|---|---|---|---|---|
| part 27 | zinc nitrate | aluminum sulfate | phosphoric acid | TEAOH | HF | $ZnO:Al_2O_3:H_3PO_4$: $R:H_2O$ = 0.5:16:32: 55:150 | 190 | 1 | 0.0506 |
| part 28 | magnesium nitrate | aluminum nitrate | phosphoric acid | TEA | | $MgO:Al_2O_3:H_3PO_4$: $R:H_2O$ = 0.5:17: 32:55:150 | 200 | 1 | 0.178 |
| part 29 | cobalt nitrate | aluminum sulfate | phosphoric acid | TEA | HF | $SiO_2:Al_2O_3:H_3PO_4$: $R:H_2O$ = 0.4:18:32: 55:150 | 170 | 0.7 | 0.255 |

III. Catalyst Preparation

The component I and the component II in the required ratio were added to the container to achieve the purposes of separation, crushing, uniform mixing and the like through one or more than two of extrusion force, impact force, shear force and friction force generated by high-speed motion of the material and/or the container, so as to realize conversion of mechanical energy, thermal energy and chemical energy by regulating the temperature and the atmosphere of carrier gas, thereby further enhancing the interaction between different components.

In the mechanical mixing process, the mixing temperature can be set as 20-100° C., and the mechanical mixing process can be conducted in an atmosphere or directly in the air. The atmosphere is selected from any of the following gas:

a) nitrogen and/or inert gas;
b) mixed gas of hydrogen, nitrogen and/or inert gas, with the volume of hydrogen in the mixed gas being 5-50%;
c) mixed gas of CO, nitrogen and/or inert gas, with the volume of CO in the mixed gas being 5-20%;
d) mixed gas of $O_2$, nitrogen and/or inert gas, with the volume of $O_2$ in the mixed gas being 5-20%, wherein the inert gas is one or more than one of helium, argon and neon.

The mechanical mixing can adopt one or more than one of mechanical agitation, ball milling, rocking bed mixing and mechanical grinding for composition. Specifically:

Mechanical stirring: mixing the component I and the component II with a stirring rod in a stirring tank; and regulating the mixing degree of the component I and the component II by controlling stirring time (5 min-120 min) and rate (30-300 r/min).

Ball milling: rolling at high speed in a grinding tank by using abrasive and the catalysts; and producing strong impact and milling on the catalysts to achieve the effects of dispersing and mixing the component I and the component II. The ratio of the abrasive (which is stainless steel, agate and quartz; and the size range is 5 mm-15 mm) to the catalysts (the mass ratio range is 20-100:1) is controlled.

Shaking table mixing: premixing the component I and the component II and placing the components into the container; realizing the mixing of the component I and the component II by controlling the reciprocating oscillation or circumferential oscillation of a shaking table; and realizing uniform mixing by regulating oscillation speed (range: 1-70 r/min) and time (range: 5 min-120 min).

Mechanical grinding: premixing the component I and the component II and placing the components into the container; and under certain pressure (range: 5 kg-20 kg), making relative motion (speed range: 30-300 r/min) by an abrader and mixed catalysts to achieve the effect of uniform mixing.

Specific catalyst preparation and parameter features are shown in Table 6.

TABLE 6

Preparation of Catalysts and Parameter Features

| | | | | Compounding Mode and Condition | | | |
|---|---|---|---|---|---|---|---|
| Catalyst Number | Component I | Component II | Weight Ratio of A to B | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
|---|---|---|---|---|---|---|---|
| A | ZnO#1 | part 1 | 0.33 | 5, 30 | | | |
| B | ZnO#2 | part 2 | 0.5 | 100, 250 | | | |
| C | ZnO#3 | part 3 | 2 | | 5 mm stainless steel ball, 50:1 | | |
| D | MnO | part 4 | 1 | | 6 mm stainless steel ball, 60:1 | | |
| E | $CeO_2$ | part 5 | 1 | | | 5, 10 | |
| F | $Bi_2O_3$ | part 6 | 3 | | | 60, 100 | |
| G | $In_2O_3$ | part 7 | 3 | | | | 5, 30 |
| H | $Ga_2O_3$ | part 8 | 1 | 100, 300 | | | |

TABLE 6-continued

Preparation of Catalysts and Parameter Features

| | | | | Compounding Mode and Condition | | | |
|---|---|---|---|---|---|---|---|
| Catalyst Number | Component I | Component II | Weight Ratio of A to B | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
| I | $ZnCr_2O_4$ | part 9 | 5 | | 6 mm agate ball, 100:1 | | |
| | $ZnAl_2O_4$ | part 10 | 1 | | | 70, 100 | |
| K | $ZnGa_2O_4$ | part 11 | 3 | | | | 15, 200 |
| L | $ZnIn_2O_4$ | part 12 | 0.33 | | | | 20, 300 |
| M | $MnCr_2O_4$ | part 13 | 1 | 100, 300 | | | |
| N | $MnAl_2O_4$ | part 14 | 3 | | 6 mm quartz, 100:1 | | |
| O | $MnZr_2O_4$ | part 15 | 0.33 | | 6 mm quartz, 100:1 | | |
| P | $MnIn_2O_4$ | part 16 | 1 | | | | 10, 100 |
| Q | $CoAl_2O_4$ | part 17 | 1 | 100, 250 | | | |
| R | $FeAl_2O_4$ | part 18 | 3 | | 5 mm stainless steel ball, 50:1 | | |
| S | $InAl_3MnO_7$ | part 19 | 1 | | | | 10, 100 |
| T | $InGa_2MnO_7$ | part 20 | 4 | | | 50, 60 | |
| U | dispersed oxide 1 | part 21 | 3 | | | | 10, 100 |
| V | dispersed oxide 2 | part 22 | 20 | | 5 mm stainless steel ball, 100:1 | | |
| W | dispersed oxide 3 | part 23 | 0.5 | 5, 30 | | | |
| X | dispersed oxide 4 | part 24 | 1 | 100, 250 | | | |
| Y | dispersed oxide 5 | part 25 | 3 | | 5 mm stainless steel ball, 50:1 | | |
| Z | dispersed oxide 6 | part 26 | 1.5 | | 6 mm stainless steel ball, 60:1 | | |
| Z1 | dispersed oxide 7 | part 27 | 2.5 | | | 5, 10 | |
| Z2 | dispersed oxide 8 | part 28 | 1.5 | | | 60, 100 | |
| Z3 | dispersed oxide 9 | part 29 | 2 | | | | 5, 30 |
| Reference example 1 | ZnO#4 | part 1 | 3 | | | 20, 30 | |
| Reference example 2 | composite metal ZnCo, the molar ratio of Zn to Co is 1:1. | part 3 | 2 | | 5 mm stainless steel ball, 50:1 | | |
| Reference example 3 | $TiO_2$ | part 3 | 2 | | 5 mm stainless steel ball, 50:1 | | |

Example of Catalytic Reactions

A fixed bed reaction was taken as an example, but the catalyst was also applicable to a fluidized bed reactor. The apparatus was equipped with gas mass flow meters and online product analysis chromatography (the tail gas of the reactor is directly connected with the metering valve of chromatography, and thus periodic and real-time sampling and analysis will be achieved).

2 g of the above catalyst in the present invention was placed in a fixed bed reactor. The air in the reactor was replaced with Ar; and then the temperature was raised to 300° C. in the $H_2$ atmosphere, and then the syngas ($H_2$/CO molar ratio=0.2-3.5) was switched. The pressure of the syngas was 0.5-10 MPa. The temperature was raised to reaction temperature of 300-600° C., and the air velocity of the reaction raw gas was regulated to 300-12000 ml/g/h. On-line chromatography was used to detect and analyze the product.

The reaction performance can be changed by changing the temperature, pressure, space velocity and $H_2$/CO molar ratio in the syngas. The sum of propylene and butylene selectivity is 30-75%. The sum of selectivity of the lower alkene, the ethylene, the propylene and the butylene is 50-90%. Due to the low hydrogenation activity of the surface of the metal composite of the catalyst, a large amount of methane will not be avoided, and the selectivity of the methane is low. Table 7 lists specific application and effect data of the catalysts.

TABLE 7

Specific Application and Effect Data of Catalysts

| Embodiment | Catalyst | GHSV(h$^{-1}$) | Temperature (° C.) | H$_2$/CO Molar Ratio | Pressure (MPa) | CO Conversion Rate % | Light Olefin Selectivity % | CH$_4$ Selectivity % | Propylene and Butylene Selectivities % |
|---|---|---|---|---|---|---|---|---|---|
| 1 | A | 3000 | 400 | 2.5 | 5 | 33.6 | 61.8 | 13.8 | 37.1 |
| 2 | B | 4000 | 410 | 1.5 | 9 | 27.5 | 62.7 | 8.4 | 42.0 |
| 3 | C | 4000 | 380 | 3 | 2.5 | 41.9 | 71.4 | 7.6 | 57.4 |
| 4 | D | 7000 | 420 | 1 | 10 | 24.5 | 74.7 | 11.8 | 60.1 |
| 5 | E | 2000 | 390 | 3.5 | 6 | 20.2 | 85.6 | 4.7 | 70.3 |
| 6 | F | 2000 | 410 | 1.5 | 3 | 40.3 | 78.4 | 8.5 | 67.7 |
| 7 | G | 3500 | 390 | 3.5 | 2.5 | 35.1 | 83.2 | 5.4 | 72.2 |
| 8 | H | 1500 | 370 | 2.5 | 5 | 19.6 | 85.1 | 4.5 | 74.7 |
| 9 | I | 2500 | 380 | 3 | 3.5 | 42.0 | 65.0 | 13.2 | 47.5 |
| 10 | J | 2000 | 410 | 2.5 | 8 | 23.3 | 84.7 | 6.4 | 71.4 |
| 11 | K | 2000 | 400 | 2.5 | 3 | 45.0 | 77.2 | 8.3 | 66.1 |
| 12 | L | 10500 | 520 | 0.5 | 1 | 35.4 | 76.0 | 10.6 | 64.6 |
| 13 | M | 3000 | 480 | 0.5 | 2 | 41.7 | 78.4 | 11.2 | 63.7 |
| 14 | N | 3000 | 470 | 0.5 | 2 | 30.4 | 80.0 | 7.4 | 70.8 |
| 15 | O | 3000 | 450 | 1 | 3 | 34.8 | 70.9 | 11.2 | 66.2 |
| 16 | P | 3000 | 450 | 1.5 | 3 | 43.5 | 65.7 | 14.8 | 43.5 |
| 17 | Q | 3000 | 350 | 3.5 | 5 | 33.0 | 62.2 | 9.6 | 44.7 |
| 18 | R | 2000 | 350 | 3 | 7 | 38.6 | 59.3 | 11.9 | 40.9 |
| 19 | S | 2500 | 400 | 1 | 6 | 19.0 | 60.8 | 11.7 | 45.7 |
| 20 | T | 4000 | 400 | 2 | 4 | 30.1 | 76.2 | 9.5 | 51.4 |
| 21 | U | 3000 | 400 | 3 | 3 | 36.1 | 67.5 | 11.1 | 43.3 |
| 22 | V | 8000 | 450 | 0.5 | 2 | 51.1 | 53.0 | 14.3 | 44.6 |
| 23 | W | 2000 | 410 | 2 | 3.5 | 11.7 | 85.3 | 2.9 | 75.0 |
| 24 | X | 3000 | 380 | 3.5 | 6 | 35.6 | 74.4 | 7.1 | 61.0 |
| 25 | Y | 5000 | 390 | 3 | 2.5 | 25.7 | 88.9 | 2.5 | 71.1 |
| 26 | Z | 4000 | 370 | 2 | 10 | 28.2 | 86.7 | 3.7 | 73.3 |
| 27 | Z1 | 10000 | 470 | 1 | 1.5 | 12.7 | 85.1 | 10.8 | 72.7 |
| 28 | Z2 | 2000 | 400 | 3.5 | 7 | 26.8 | 67.7 | 12.3 | 45.7 |
| 29 | Z3 | 3000 | 380 | 1.5 | 2.5 | 41.3 | 55.3 | 14.2 | 43.1 |
| 38 | Reference example 1 | 3000 | 320 | 0.5 | 1 | 1.9 | 31.0 | 31.0 | 29.2 |
| 39 | Reference example 2 | 4000 | 450 | 3 | 3 | 30.5 | 26.8 | 22.6 | 12.9 |
| 40 | Reference example 3 | 2000 | 350 | 2.5 | 3 | 0.3 | 25.5 | 65.1 | 19.4 |
| 41 | Reference example 4 | 2000 | 410 | 1.5 | 3 | 24.6 | 46.2 | 9.7 | 25.6 |
| 42 | Reference example 5 | 3000 | 400 | 2 | 3.5 | 31.2 | 19.5 | 10.8 | 12.7 |
| 43 | Reference example 6 | 3000 | 450 | 2.5 | 4 | 8.3 | 1.5 | 50 | 0.7 |
| 44 | Reference example 7 | 2200 | 450 | 3 | 2 | <1 | — | — | — |

In reference example 1, the catalyst component I is ZnO#4, and component II is part 1. The zeolite in the catalyst adopted in reference example 4 is a commodity SAPO-34 purchased from Nankai University Catalyst Factory, wherein the temperature of desorption peak of mediate strong acid on NH3-TPD is 390° C. and the amount of the mediate strong acid sites is 0.6 mol/kg. The zeolite in the catalyst adopted in reference example 5 is a commodity ZSM-5 purchased from Nankai University Catalyst Factory, wherein the zeolite is of a full microporous structure, and the silica alumina ratio is 30.

Reaction results of reference examples 4 and 5 show that, the topology and acid strength of CHA or AEI are crucial to the selective modulation of the products.

The catalyst adopted in reference example 6 is a sample containing only component IZnO#1 without the zeolite, and the reaction conversion rate is very low. The products mainly comprise by-products such as dimethyl ether and methane, and almost no ethylene is produced.

The catalyst adopted in reference example 7 is a sample containing only component II and part 1 zeolite without the component I, and the catalytic reaction almost has no activity.

Reference examples 6 and 7 have extremely poor reaction effects when only containing component I or component II on the surface, and do not have the excellent reaction performance described in the present invention.

In the reference technology of the document (Jiao et al., Science 351 (2016) 1065-1068), the acid amount of the used SAPO-34 zeolite is large. The acid amount of the mediate strong acid reaches 0.32 mol/kg according to the NH3-TPD test. Therefore, when the conversion rate is increased to 35%, alkene selectivity is 69%, alkane selectivity is 20%, alkene/alkane ratio is decreased to 3.5 and propylene and butylene selectivity is 40-50%.

It is observed that from the above table that, the structure of the zeolite including the topologies, acid strength and acid amount of CHA&AEI, and the matching between the metal oxide and the zeolite are crucial and directly affect the conversion rate of carbon monoxide and propylene and butylene selectivity.

The invention claimed is:

1. A catalyst, comprising a component I and a component II, which are compounded in a mechanical mixing mode; an ingredient of the component I being a metal oxide; the component II being a zeolite of CHA or AEI topology; wherein, the metal oxide is at least one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$;

a specific surface area of $MnO_x$, $ZnO_x$, $CeO_x$, $GaO_x$, $BiO_x$ and $InO_x$ is 1-100 $m^2/g$;

a specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn_{(1-a-b)}O_x$, and $In_aGa_bMn_{(1-a-b)}O_x$ is 5-150 $m^2/g$;

a value range of x is 0.7-3.7, and a value range of a is 0-1; and a value range of a+b is 0-1;

the zeolite of CHA or AEI topology comprises eight-membered ring orifices, a three-dimensional porous channel, and CHA cage; and the zeolite of CHA or AEI topology comprises mediate strong acid sites in an amount of 0.003-0.06 mol/kg.

2. The catalyst according to claim 1, wherein the skeleton element composition of the zeolite of CHA or AEI topology is at least one of Si—O, Si—Al—O, Si—Al—P—O, Al—P—O, Ga—P—O, Ga—Si—Al—O, Zn—Al—P—O, Mg—Al—P—O, and Co—Al—P—O.

3. The catalyst according to claim 1, wherein a weight ratio of the ingredients in the component I to the component II is 0.1-20.

4. The catalyst according to claim 1, wherein the dispersing agent is also added to the component I; the metal oxide is dispersed in the dispersing agent; the dispersing agent is at least one of $Al_2O_3$, $SiO_2$, $Cr_2O_3$, $ZrO_2$, $TiO_2$, $Ga_2O_3$, activated carbon, graphene, and carbon nanotube; in the component I, the content of the dispersing agent is 0.05-90 wt %, and the balance is the metal oxide.

5. The catalyst according to claim 1, wherein H is connected or not connected to O element of the zeolite skeleton.

6. The catalyst according to claim 5, wherein, when H is connected to O element of the zeolite skeleton, the H is entirely or partially replaced by at least one of Na, Ca, K, Mg, Ge, Zr, Zn, Cr, Ga, Sn, Fe, Co, Mo and Mn by ion exchange, and the total molar ratio of the substitute metal to oxygen is 0.0002-0.001.

7. A method for preparing light olefin via direct conversion of syngas comprising converting the syngas to the light olefin in the presence of the catalyst of claim 1.

8. The method according to claim 7, wherein the converting is conducted under a pressure of 0.5-10 MPa, a reaction temperature of 300-600° C., and a space velocity of 300-12000 $h^{-1}$, and the syngas is a $H_2/CO$ mixture with a ratio of $H_2/CO$ of 0.2-3.5.

9. The method according to claim 7, wherein the light olefin is $C_{2-4}$ olefin, and the method achieves a selectivity for $C_{2-4}$ olefin of 50-90%, and a selectivity for a methane side product of lower than 15%.

10. The catalyst according to claim 1, wherein the specific surface area of $MnO_x$, $ZnO_x$, $CeO_x$, $GaO_x$, $BiO_x$ and $InO_x$ is 50-100 $m^2/g$, and the specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn_{(1-a-b)}O_x$, and $In_aGa_bMn_{(1-a-b)}O_x$ is 50-150 $m^2/g$.

11. The catalyst according to claim 3, wherein the weight ratio of the ingredients in the component I to the component II is 0.3-5.

12. The method according to claim 7, wherein the converting is conducted under a pressure of 1-8 MPa; a reaction temperature of 350° C.-450° C., and a space velocity of 1000-9000 $h^{-1}$, and the syngas is a $H_2/CO$ mixture with a ratio of $H_2/CO$ of 0.3-2.5.

13. The method according to claim 12, wherein the space velocity is 3000-9000 $h^{-1}$.

14. The catalyst according to claim 1, wherein the skeleton element composition of the zeolite of CHA or AEI topology is at least one of Si—Al—P—O, Al—P—O, Ga—P—O, Zn—Al—P—O, Mg—Al—P—O, and Co—Al—P—O.

* * * * *